(12) United States Patent
Franer et al.

(10) Patent No.: US 7,967,791 B2
(45) Date of Patent: Jun. 28, 2011

(54) SURGICAL ACCESS DEVICE (75) Inventors: Paul T. Franer, Cincinnati, OH (US);
Timothy P. Lessek, Mason, OH (US);
Victor C. Moreno, Terrace Park, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 286 days.

(21) Appl. No.: 11/781,645

(22) Filed: Jul. 23, 2007

(65) Prior Publication Data
US 2009/0030375 A1    Jan. 29, 2009

(51) Int. Cl.
*A61M 5/178* (2006.01)
(52) U.S. Cl. .................................................. 604/167.06
(58) Field of Classification Search . 604/167.01–167.06
See application file for complete search history.

(56) References Cited

U.S. PATENT DOCUMENTS

| | | | |
|---|---|---|---|
| 7,163,525 B2 | 1/2007 | Franer | |
| 2004/0230161 A1* | 11/2004 | Zeiner | 604/167.06 |
| 2005/0059934 A1* | 3/2005 | Wenchell et al. | 604/167.01 |
| 2005/0077688 A1 | 4/2005 | Voegele et al. | |
| 2006/0135972 A1 | 6/2006 | Zeiner | |
| 2006/0135977 A1 | 6/2006 | Thompson et al. | |
| 2006/0211992 A1* | 9/2006 | Prosek | 604/167.06 |
| 2007/0255218 A1 | 11/2007 | Franer | |
| 2008/0097294 A1* | 4/2008 | Prather et al. | 604/95.04 |

* cited by examiner

*Primary Examiner* — Nicholas D Lucchesi
*Assistant Examiner* — Pritesh Patel
(74) *Attorney, Agent, or Firm* — Nutter McClennen & Fish LLP (57) ABSTRACT

Methods and devices for accessing a body cavity are disclosed. In general, a surgical access device is provided that can include a cannula that defines a working channel that is sized and configured to receive a surgical instrument. A seal can be disposed in the cannula of the surgical access device. In one exemplary embodiment, the seal can be positioned at a point in the cannula that is effective to maintain contact between the seal and an instrument inserted therethrough as the instrument is rotated about that point.

8 Claims, 8 Drawing Sheets

SURGICAL ACCESS DEVICE

FIELD OF THE INVENTION

The present invention relates to methods and devices for accessing a body cavity.

BACKGROUND OF THE INVENTION

Minimally invasive surgical procedures including, for example, endoscopic, laparoscopic, and arthoscopic procedures, allow a surgeon to perform a complex surgical procedure with minimal incisions into the skin and tissue surrounding a particular body cavity or anatomical region. In order to gain access to a body cavity, it is often necessary to puncture and cannulate the body cavity using a surgical access device such as a trocar. A trocar assembly generally includes a trocar housing with a cannula extending therefrom and a trocar obturator that is inserted through the cannula. In use, the trocar cannula, with the obturator extending therethrough, is pierced through the skin to access a body cavity. To penetrate the skin, the distal end of the trocar cannula is placed against an incision in the skin and pressure is applied to the proximal end of the trocar to force the sharp point of the obturator through the skin until it enters the targeted body cavity. The obturator can then be withdrawn, leaving the cannula as an access way to the targeted body cavity.

Generally, the proximal end of the trocar cannula is joined to a trocar housing that defines a chamber having an open distal end portion in communication with the interior lumen defined by the trocar cannula. The trocar oburator, as well as other elongated surgical instruments or tools, axially extend into and are withdrawn from the trocar cannula through the proximal end portion of the chamber defined by the trocar housing.

In use, it is important to maintain a substantially closed environment during insertion or withdrawal of instruments through the trocar assembly so as to preserve sterility of the treatment site in addition to preventing the escape of liquids and/or insufflation gas. Typically, a seal element is disposed within the housing in an attempt to provide such an environment. However, if an instrument is delivered off-axis relative to the cannula, the effectiveness of the seal may diminish, as off-axis delivery results in a disproportionate force being applied to one portion of the seal. This can result in non-uniform deformation of the seal which can reduce the seal's ability to effectively engage an outer surface of an instrument thereby resulting in contamination of the site and/or escape of liquids and/or insufflation gas from the cannula. Seal deformation can also be caused by inserting an instrument with a relatively large diameter through a seal having a relatively small diameter. In addition to deforming the seal, forcing a large diameter instrument through a relatively small diameter seal can result in a significant increase in the normal force subjected to the shaft of the instrument. The surgeon feels this increased force as increased drag or resistance to the instrument insertion/movement.

Accordingly, there remains a need for devices and methods configured to allow for the efficient and reliable delivery of a surgical instrument to a treatment site.

SUMMARY OF THE INVENTION

The present invention generally provides devices and methods for accessing a body cavity. In general, a surgical access device is provided that includes a cannula that defines a working channel that is sized and configured to receive a surgical instrument. The surgical access device can also include a seal assembly. The seal assembly can generally be positioned in the cannula of the surgical access device. In one exemplary embodiment, the seal can be positioned at a point in the cannula that is effective to maintain contact between the seal and an instrument inserted therethrough as the instrument is rotated about that point. This point can be characterized as the neutral point of the instrument (i.e., the pivot point or point about which an instrument is pivoted).

A variety of configurations are available for the seal assembly. For example, the seal assembly can take the form of a zero-closure seal such as a multi-layer, conical shaped seal. In one exemplary embodiment, the seal can form at least a portion of a sidewall of the cannula. The portion of the sidewall formed by the seal can be adapted to expand radially upon insertion of a large instrument through the cannula.

In another embodiment, a housing can be coupled to a proximal end of the cannula. In one exemplary embodiment, the surgical access device can include a first seal assembly that is disposed in the housing and a second seal assembly that is disposed in the cannula. A variety of seal assemblies can be combined to make up the seals disposed in the housing and cannula of the trocar assembly. For example, in one embodiment, a duckbill seal can be disposed in the housing and a fan seal can be disposed in the cannula. The second seal assembly can generally be positioned at the neutral point of the cannula, the neutral point being the point about which an instrument inserted through the cannula is rotated. In an exemplary embodiment, the second seal assembly can be integrally formed with the cannula such that the seal forms at least a portion of the a sidewall of the cannula. As with the single seal embodiment, the portion of the sidewall that is formed by the seal can also be adapted to expand radially upon insertion of a large instrument through the cannula.

The surgical seal assembly can further include an obturator that is adapted to be slidably and removably extendable through the working channel of the cannula. In an exemplary embodiment, the obturator can have a notch in a sidewall thereof. The notch can be positioned to align with the seal assembly disposed in the cannula upon insertion of the obturator through the cannula such that the seal is not deflected when the obturator is present.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Disclosed herein are methods and devices for accessing a body cavity. In general, a surgical access device is provided that can include a cannula that defines a working channel that is sized and configured to receive a surgical instrument. A seal can be disposed in the cannula of the surgical access device. In one exemplary embodiment, the seal can be positioned at a point in the cannula that is effective to maintain contact between the seal and an instrument inserted therethrough as the instrument is rotated about that point.

Figure 1:
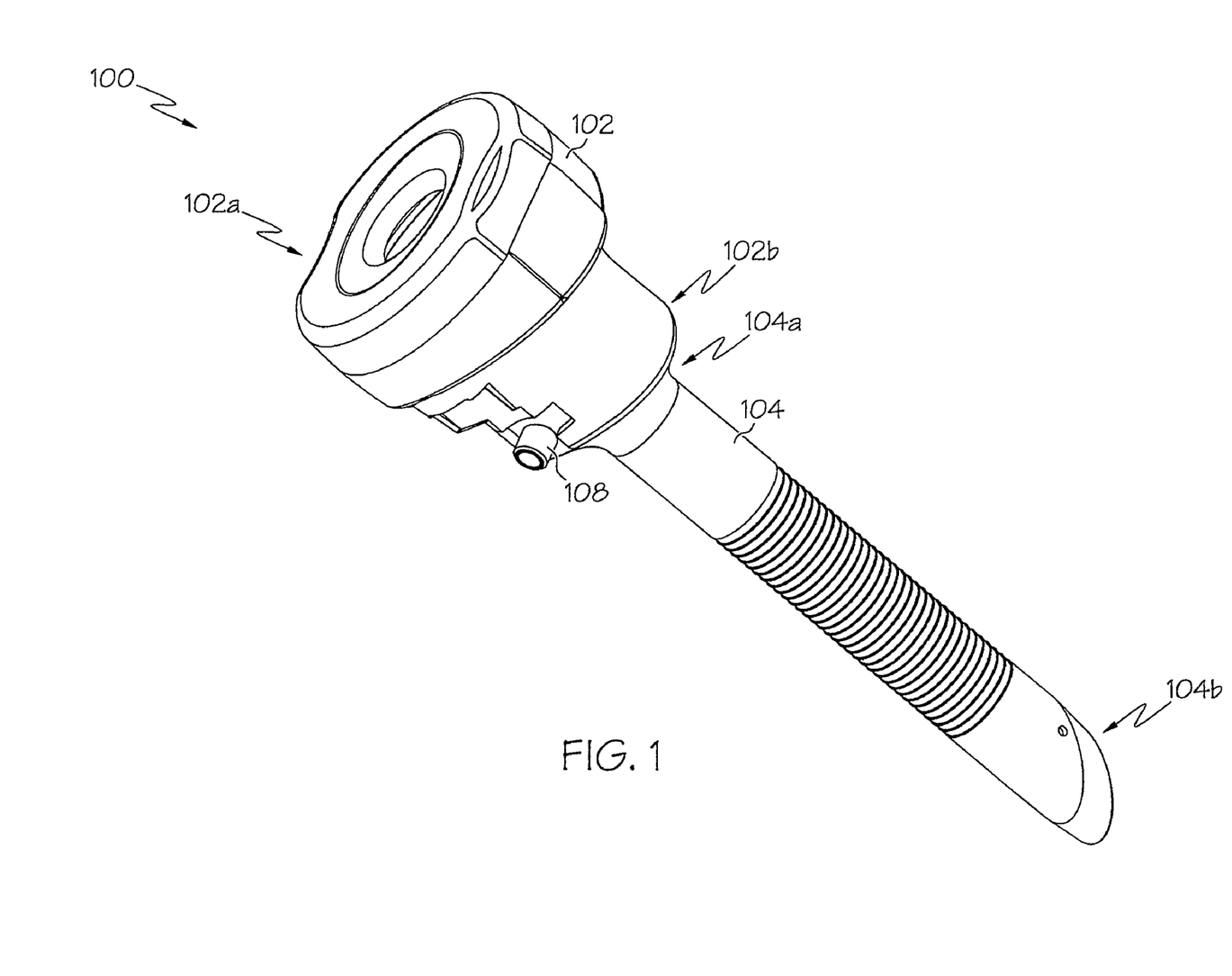
FIG. 1 is a perspective view of one embodiment of a surgical access device for accessing a body cavity.

FIG. 1 illustrates one exemplary embodiment of a surgical access device 100. As shown, the surgical access device 100 generally includes a housing 102 with a cannula 104 that extends distally therefrom. Although the surgical access device is shown and described as having a housing coupled to a proximal end of a cannula, the device need not include a housing and, in one exemplary embodiment, can be defined solely by the cannula. The housing 102 can have an open proximal end portion 102a and an open distal end portion 102b. The proximal end portion 102a can define an opening that is adapted to receive an instrument, and the distal end portion 102b can be configured to mate to or be coupled to a proximal end 104a of the cannula 104. Similar to the housing 102, the cannula 104 can also have an open distal end portion 104b and an open proximal end portion 104a. The proximal end portion 104a can extend into and be mounted or otherwise coupled to the open distal end 102b of the housing 102. The cannula 104 can extend distally from the housing 102 to define an inner lumen or working channel 106 (FIG. 2) that is sized and configured to receive a surgical instrument. One skilled in the art will appreciate that the housing 102 and cannula 104 can be formed as a unitary structure or as two separate components that are mated to one another. The housing 102 can also include a stop-cock valve 108 for allowing and preventing the passage of an insufflation fluid, e.g. carbon dioxide, through flexible tubing (not shown) and into a portion of the housing 102 and cannula 104.

Figure 2:
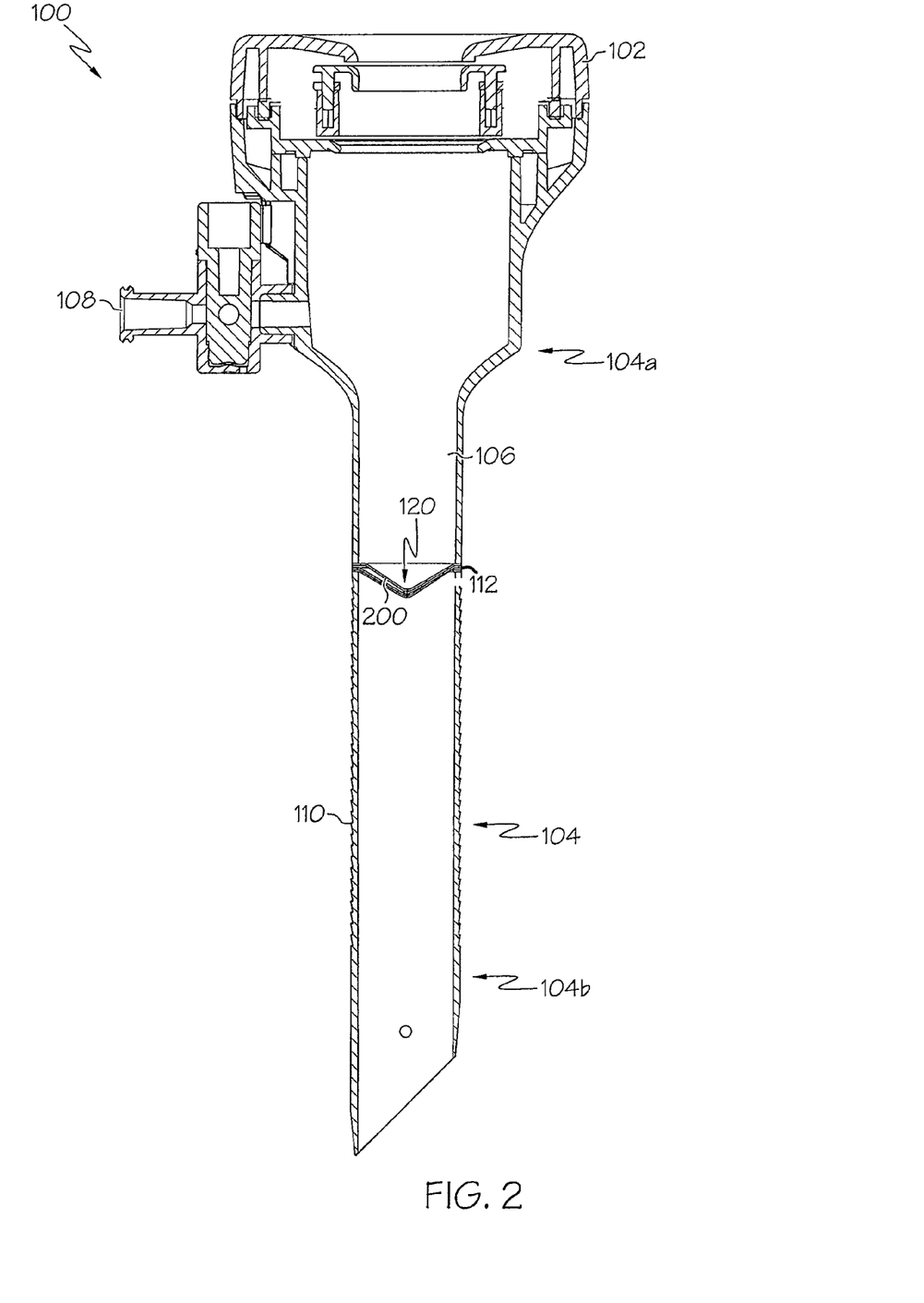
FIG. 2 is a cross-sectional view of the surgical access device shown in FIG. 1.
Figure 2A:
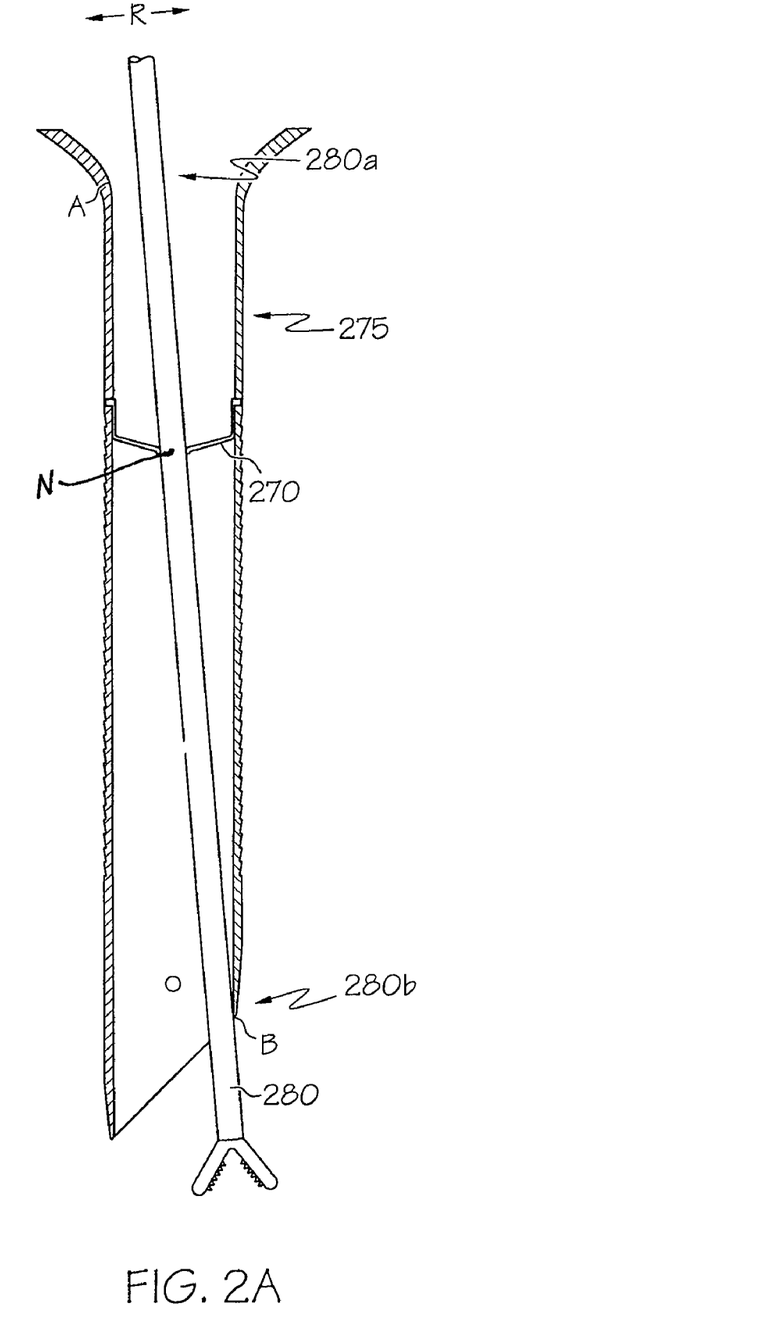
FIG. 2A is a cross-sectional view of another embodiment of a surgical access device showing an instrument disposed therethrough.

As indicated above, the surgical access device can also include a seal assembly. In one exemplary embodiment, shown in FIGS. 2 and 2A, the surgical access device 100 includes a single seal assembly 200 that is disposed in the cannula 104. In general, the seal assembly 200 can be positioned at an axial position, such as point 120, in the cannula 104 that is effective to maintain contact between the seal 200 and an instrument inserted therethrough as the instrument is rotated or pivoted about point 120. This point 120 (i.e., the pivot point or point about which an instrument is pivoted) can correspond to the neutral point N of the instrument 280 (FIG. 2A). The neutral point N of the instrument 280 is the point that will remain stationary or neutral with respect to the cannula when the instrument is rotated or pivoted about this point in the manner indicated by arrows R in FIG. 2A. Positioning the seal assembly 200 at the neutral point of the instrument can be effective to reduce any radial displacement of the instrument with respect to the center of the cannula 104 during manipulation of the instrument.

The neutral point can generally be determined by finding a midpoint or mid-range between the proximal and distal contact points of the cannula and an instrument disposed therethrough when the instrument is rotated as indicated by arrows R. For example, as shown in FIG. 2A, when the instrument 280 is rotated to one extreme position a proximal portion 280a of the instrument 280 contacts the cannula 275 at proximal contact point A and a distal portion 280b of the instrument 280 contacts the cannula 275 at a distal contact point B. The neutral point N is, thus, positioned at or near the midpoint between proximal and distal contact points A and B. Because the neutral point may vary between instruments (i.e., the proximal and distal contact points may vary with the size and shape of the instrument), the seal assembly 270 need not be positioned at a specific midpoint for a particular instrument. Instead, a mid-range can be determined for a number of instruments, and the seal assembly can be positioned within that mid-range. The neutral point may also vary if the surgical access device has an angled proximal end. In particular, the distance between the proximal and distal contact points (i.e., the contact length) may vary as an instrument is rotated in a radial fashion around a surgical access device having an angled proximal end. In such a configuration, the neutral point can be determined by finding a nominal midpoint that is positioned between the midpoints that correspond to the varying contact lengths.

Figure 4:
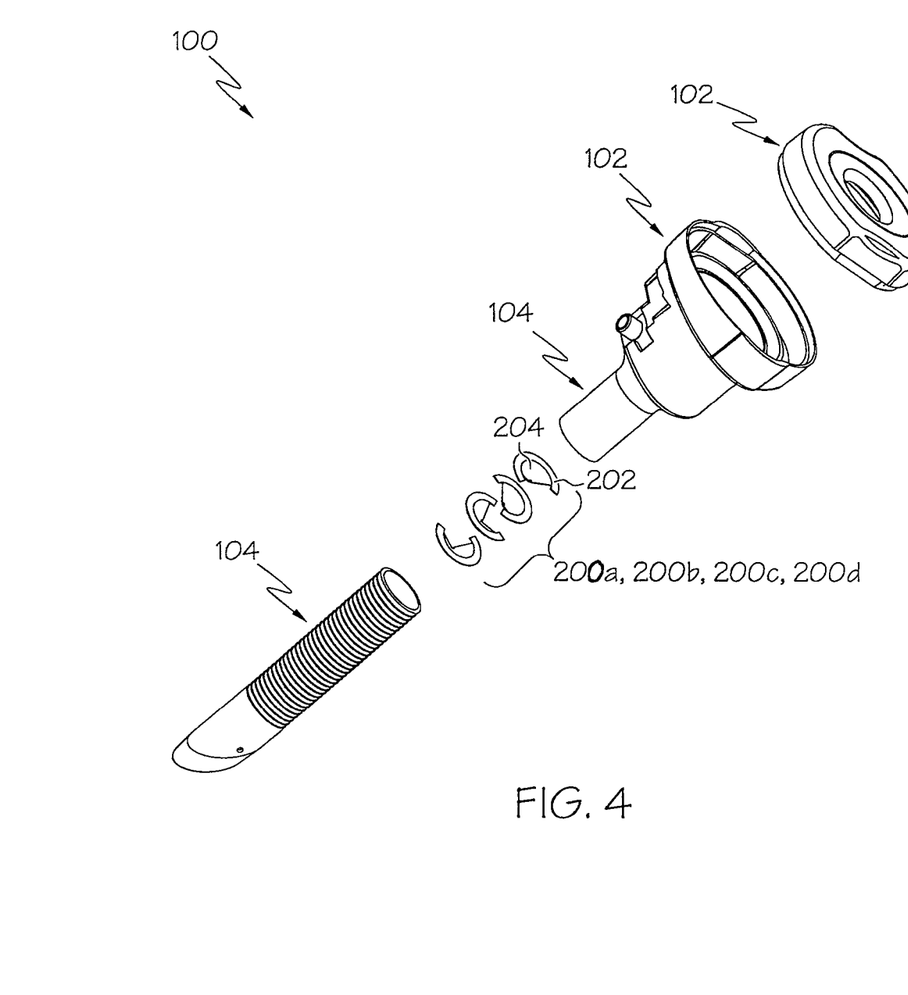
FIG. 4 is an exploded view of the surgical access device shown in FIG. 1.
Figure 6A:
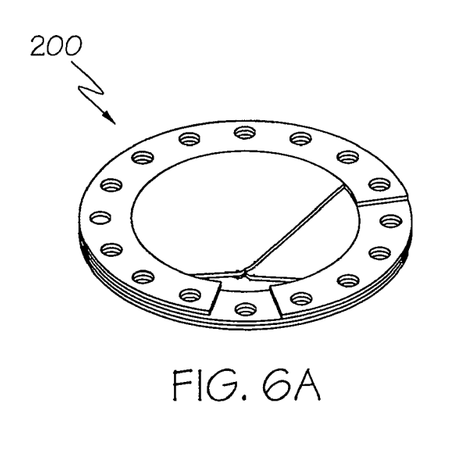
FIG. 6A is a perspective view of one embodiment a zero-closure seal.

A variety of configurations are available for the seal assembly 200. In general, the seal assembly 200 can take the form of a zero-closure seal, as such a seal assembly 200 can facilitate sealing both with and without an instrument present in the surgical access device 100 without the need for a second seal assembly. In an exemplary embodiment shown in FIGS. 2, 4, and 6A, the seal assembly 200 takes the form of a multi-layer conical shaped, zero-closure seal. The conical shaped, zero-closure seal 200 can include a series of overlapping seal segments 200a, 200b, 200c, 200d (FIG. 4) that are assembled in a woven arrangement to provide a complete seal body. As shown in FIG. 4, four seal segments 200a, 200b, 200c, 200d are arranged to create the seal assembly. While FIG. 4 illustrates a seal assembly 200 formed from four seal segments 200a, 200b, 200c, 200d, one skilled in the art will appreciate that the seal assembly 200 can be formed from any number of seal segments. The seal segments can generally include a proximal flange portion 202 with a semi-circular profile and an inwardly extending tapered portion 204 that extends distally therefrom. The seal segments 200a, 200b, 200c, 200d can be stacked on top of one another or woven together in an overlapping fashion to form the multi-layer conical shaped seal 200 shown in FIGS. 2 and 6A. In use, an instrument can be inserted into the center of the seal assembly 200 and the seal segments 200a, 200b, 200c, 200d can engage an outer surface of the instrument to thereby prevent the passage of fluids through the housing 102.

The seal segments 200a, 200b, 200c, 200d can be made from any number of materials known to those skilled in the art including, but not limited to, polyisoprene and silicone. The seal segments 200a, 200b, 200c, 200d can also be molded such that they have a varying thickness across the profile of the seal 200. Varying the thickness across to the profile of the seal can be effective to minimize leakage and reduce drag forces on the instrument. Exemplary seal assembly embodiments are further described in U.S. Publication No. 2004/0230161, titled "Trocar Seal Assembly," filed on Mar. 31, 2004, and U.S. application Ser. No. 10/687,502, titled "Conical Trocar Seal," filed on Oct. 15, 2003, which are hereby incorporated by reference in their entirety.

Several techniques can be used to incorporate the multi-layer conical shaped seal 200 into the cannula 104 of the surgical access device 100. For example, the seal can be mated or affixed to an inner wall of the cannula as shown in FIG. 2A. Alternatively, as illustrated in FIG. 2, the seal assembly 200 can be integrally formed with the cannula 104 such that the seal 200 forms at least a portion 112 of a sidewall 110 of the cannula 104. The portion 112 of the sidewall 110 formed by the seal 200 can be adapted to expand radially upon insertion of a large instrument (i.e., an instrument having a diameter that is large relative to the diameter of the cannula) through the cannula. Radial expansion of the sidewall 112 can be effective to increase abdominal wall retention in addition to reducing the drag force applied to an instrument by the seal assembly 200. Integrally forming the seal assembly 200 with the cannula 104 can also allow the portion 112 of the sidewall 110 of the cannula 104 formed by the seal 200 to be flexible. A variety of techniques can be used to form the seal assembly 200 with the cannula 104. For example, in one embodiment, the cannula 104 can be split into two pieces and the seal assembly 200 can be trapped therebetween utilizing techniques such as sonic welding and adhesives. In another embodiment, the seal assembly and the cannula can be manufactured simultaneously to form one unitary structure.

Figure 3:
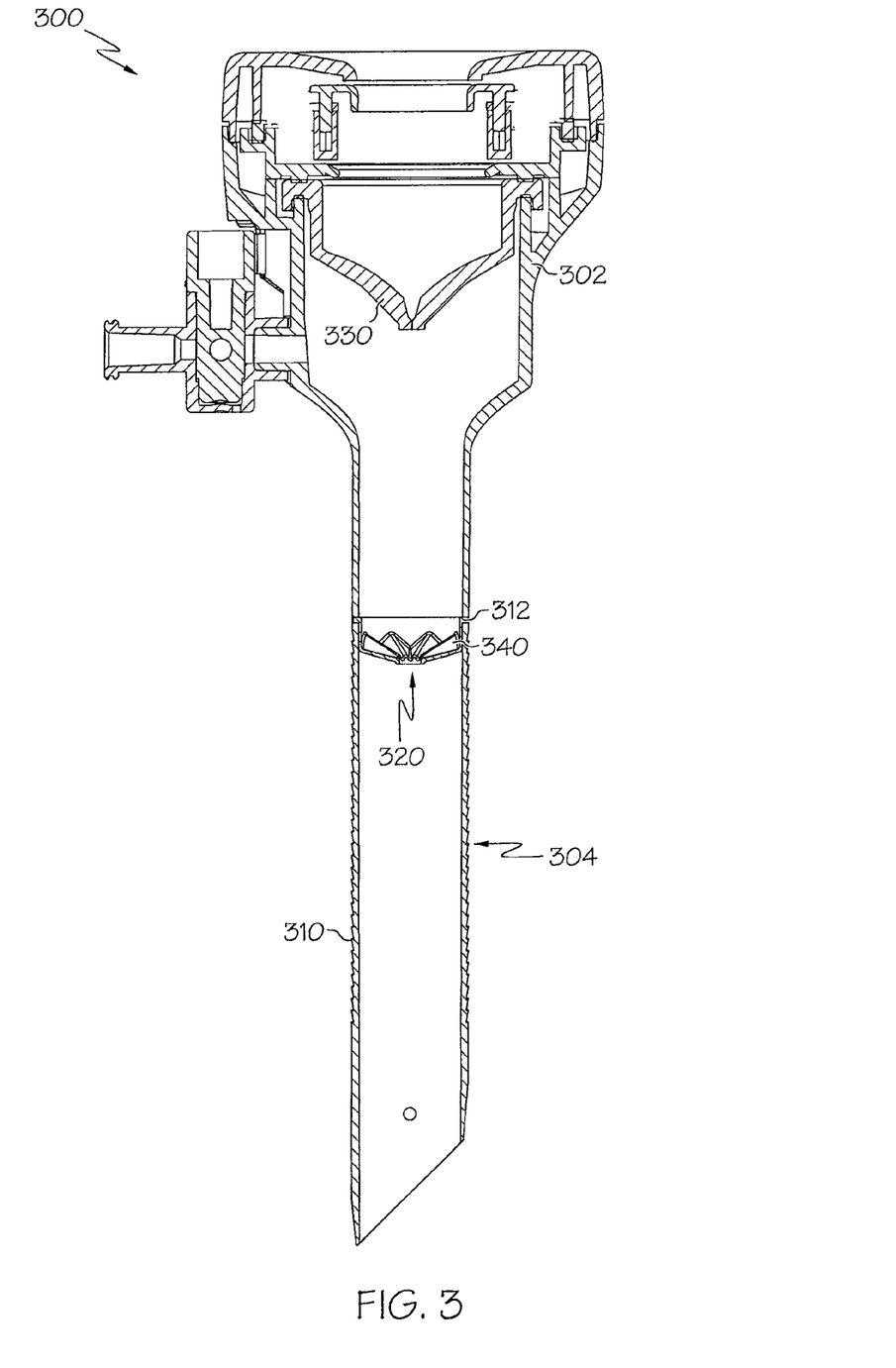
FIG. 3 is a cross-sectional view of another embodiment of a surgical access device for accessing a body cavity.
Figure 5:
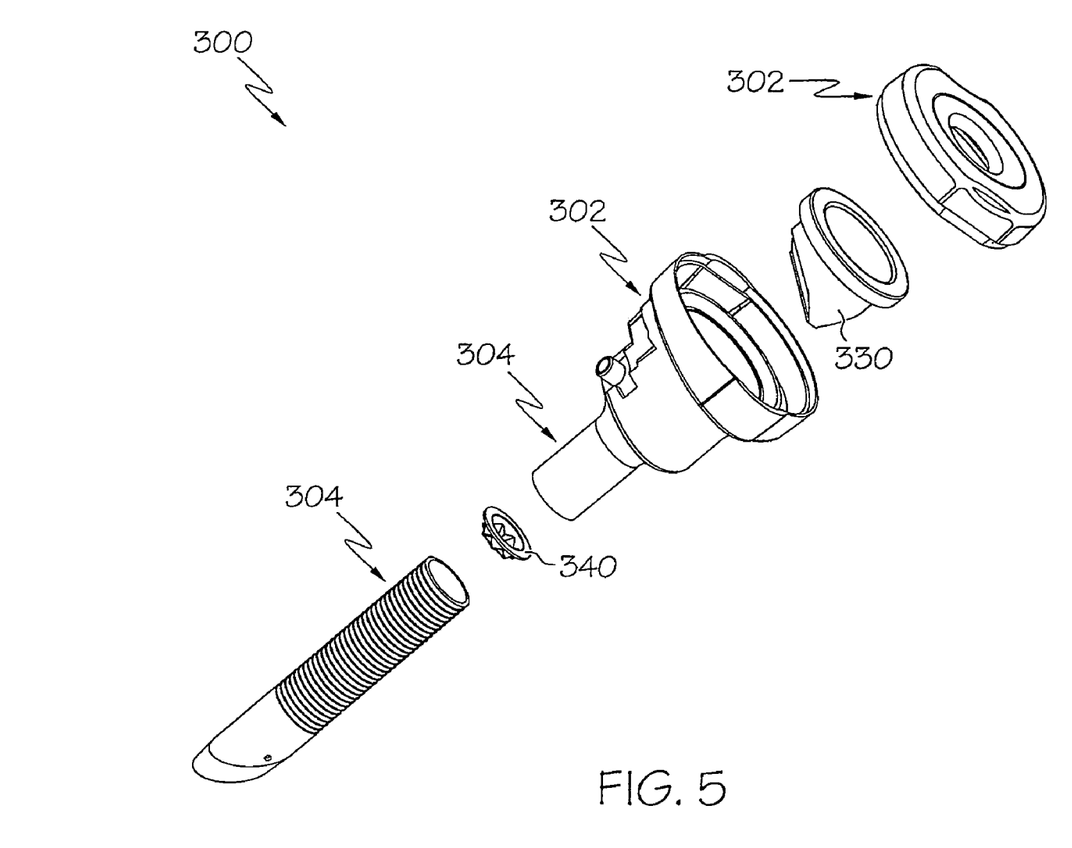
FIG. 5 is an exploded view of the surgical access device shown in FIG. 3.
Figure 6B:
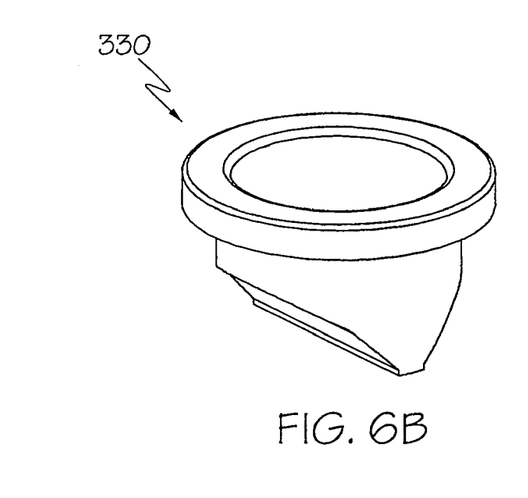
FIG. 6B is a perspective view of one embodiment a duckbill seal.
Figure 6C:
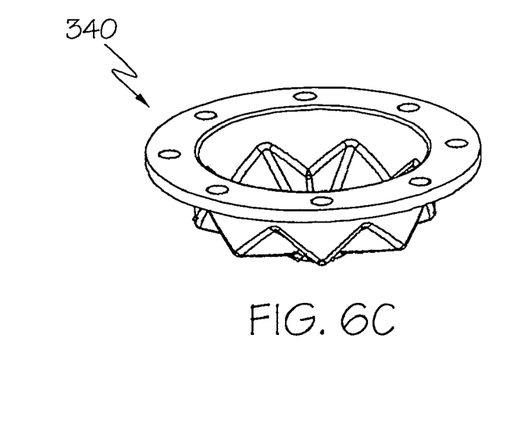
FIG. 6C is a perspective view of one embodiment of a fan seal.

FIGS. 3 and 5 illustrate another exemplary embodiment of a surgical access device 300. As shown, the surgical access device 300 includes a first seal assembly 330 that is disposed in the housing 302 and a second seal assembly 340 that is disposed in the cannula 304. A variety of seal assemblies can be combined to make up the seals disposed in the housing 302 and cannula 304 of the surgical access device 300. For example, as shown in FIGS. 3 and 5, a duckbill seal 330 (FIG. 6B) can be disposed in the housing 302 and a fan seal 340 (FIG. 6C) can be disposed in the cannula 304. Similar to the embodiment described above, the second seal assembly 340 can be positioned at the neutral point 320 of the cannula to reduce any radial displacement of an instrument inserted therethrough. The second seal assembly 340 can also be integrally formed with the cannula 304 to allow radial expansion of the portion 312 of the sidewall 310 formed by the seal assembly 340. The duckbill or first seal 330 can be adapted to seal the surgical access device 300 when no instrument is present and the fan or second seal 340 can be adapted to seal around an instrument that is present in the surgical access device 300. Because the surgical access device 300 includes first and second seal assemblies 330, 340, the second seal assembly 340 need not be a zero-closure seal. Thus, virtually any type of seal (including zero-closure seals, such as the seal shown in FIG. 6A, as well as other types of seals) can be disposed in the cannula 304.

Figure 7:
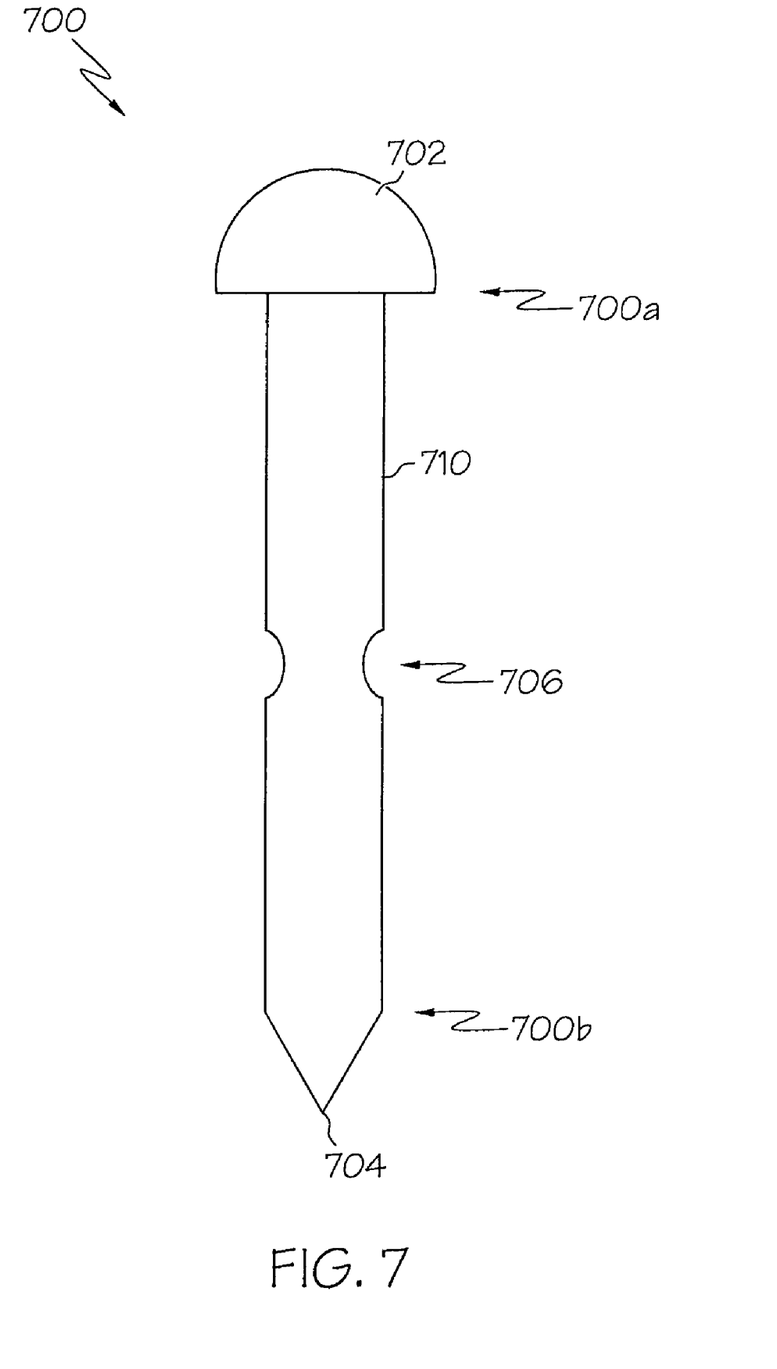
FIG. 7 is a perspective view of one embodiment of an obturator.

The surgical access device can further include an obturator. FIG. 7 illustrates one exemplary embodiment of an obturator 700 for use with the surgical access device described herein. As shown, the obturator 700 is a generally elongate member that is adapted to be slidably and removably extendable through the working channel of the cannula. The obturator can have a handle 702 that is disposed at a proximal end 700a thereof to facilitate manipulation of the obturator 700. A blade 704 for piercing tissue to access a treatment site can be disposed at a distal end 700b of the obturator 700. As illustrated in FIG. 7, the obturator 700 can include a notch 706 formed in a sidewall 710 thereof. The notch 706 can be positioned in a manner such that it is aligned with a seal assembly disposed in the cannula upon insertion of the obturator through the working channel of the surgical access device. While a number of configurations are available, the notch 706 can generally be sized and shaped to seat the seal assembly such that the seal is not deflected when the obturator 700 is present. Such a configuration can allow the obturator 700 to be inserted through the surgical access device for packaging while reducing the risk of the seal undergoing stress, relaxation, and/or creep as a result of a force applied to the seal by the obturator 700. This configuration can also allow for the surgical access device and obturator construct to pierce the abdominal wall without any additional friction from a deflected seal.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used device is obtained and if necessary cleaned. The device can then be sterilized. In one sterilization technique, the device is placed in a closed and sealed container, such as a plastic or TYVEK bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical access device, comprising;
A cannula that defines a working channel sized and configured to receive a surgical instrument; and
a zero-closure seal disposed in the cannula and positioned at a point that is effective to maintain contact between the seal and an instrument inserted therethrough as the instrument is rotated about the point, wherein the point is approximately a midpoint between proximal distal contact points of the cannula and the instrument disposed therethrough; and wherein the seal forms at least a portion of a sidewall of the cannula; and wherein the portion of the sidewall formed by the seal is adapted to expand radially upon insertion of a large instrument through the cannula.

2. The surgical access device of claim 1, further comprising a housing coupled to a proximal end of the cannula.

3. The surgical access device of claim 2, further comprising a second seal disposed in the housing.

4. The surgical access device of claim 3, wherein the second seal is a duckbill seal.

5. The surgical access device of claim 1, further comprising an obturator having a notch in a sidewall thereof, the notch being positioned to align with the seal upon insertion of the obturator through the cannula such that the seal is not deflected when the obturator is present.

6. A surgical access device, comprising:

a proximal portion that defines a working channel having a first diameter;

a cannula distally extending from the proximal portion and having a single seal disposed therein, wherein the seal forms at least a portion of a sidewall of the cannula; wherein the seal forms at least a portion of the sidewall of the cannula; wherein the portion of the sidewall formed by the seal is adapted to expand radially upon insertion of a large instrument through the cannula;

wherein the single seal is disposed in the cannula and positioned at a point that is effective to maintain contact between the seal and an instrument inserted therethrough as the instrument is rotated about the point, wherein the point is approximately a midpoint between proximal distal contact points of the cannula and the instrument disposed therethrough;

wherein the cannula defines a working channel in communication with the working channel of the proximal portion and having a second diameter that is smaller than the first diameter, the cannula being sized and configured to receive a surgical instrument.

7. The surgical access device of claim 6, wherein the seal is a zero-closure seal.

8. The surgical access device of claim 6, further comprising an obturator having a notch in a sidewall thereof, the notch being positioned to align with the seal upon insertion of the obturator through the cannula such that the seal is not deflected when the obturator is present.

* * * * *